(12) United States Patent
Bhatia et al.

(10) Patent No.: US 10,583,048 B1
(45) Date of Patent: *Mar. 10, 2020

(54) FLUID DETECTION SYSTEM

(71) Applicant: Theos Medical Systems, Santa Clara, CA (US)

(72) Inventors: Saket Bhatia, Santa Clara, CA (US); Ankush Bhatia, Vancouver (CA)

(73) Assignee: Theos Medical Systems, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/641,220

(22) Filed: Jul. 4, 2017

Related U.S. Application Data

(63) Continuation of application No. 14/958,949, filed on Dec. 4, 2015, now Pat. No. 9,782,303, which is a continuation of application No. 13/925,859, filed on Jun. 25, 2013, now Pat. No. 9,261,231.

(51) Int. Cl.
*A61F 13/42* (2006.01)

(52) U.S. Cl.
CPC ........ *A61F 13/42* (2013.01); *A61F 2013/424* (2013.01)

(58) Field of Classification Search
CPC .......... A61F 13/42; A61F 13/15; A61F 13/16; A61F 13/20; A61F 13/422; A61F 13/424; A61F 13/426; A61F 13/494; G08B 21/00; G08B 21/20

USPC .......... 340/539.1, 539.11, 573.4, 573.5, 604; 600/300, 301, 438; 604/385.01, 361; 128/885, 886

See application file for complete search history.

(56) References Cited

U.S. PATENT DOCUMENTS

| | | | | |
|---|---|---|---|---|
| 5,790,036 A | * | 8/1998 | Fisher | A61F 13/42 128/886 |
| 7,250,547 B1 | * | 7/2007 | Hofmeister | A61F 13/42 340/573.5 |
| 2011/0028803 A1 | * | 2/2011 | Ollmar | A61B 5/0531 600/301 |
| 2013/0165780 A1 | * | 6/2013 | Tamada | A61B 8/04 600/438 |

* cited by examiner

*Primary Examiner* — Hung T Nguyen

(57) ABSTRACT

Disclosed is a fluid detection device including a fluid sensor positioned near a patient's body and providing a signal whether the sensor detects fluid from the patient's body; a casing surrounding the alarm and allowing the signal to be sensed by the patient; an alarm coupled to the fluid sensor, the alarm including one or more of: an audible signal sensible by the patient, a haptic signal sensible by the patient, a visible signal sensible by the patient through the casing; a casing surrounding the alarm and allowing the signal to be sensed by the patient; and a fastener coupled to the casing, adjustable to attach and remove from one or more of: the patient's body, the patient's clothing. The casing, when closed, may couple a power source to the alarm. Also included may be a human interface and other features. Also disclosed is a fluid detection method.

15 Claims, 5 Drawing Sheets

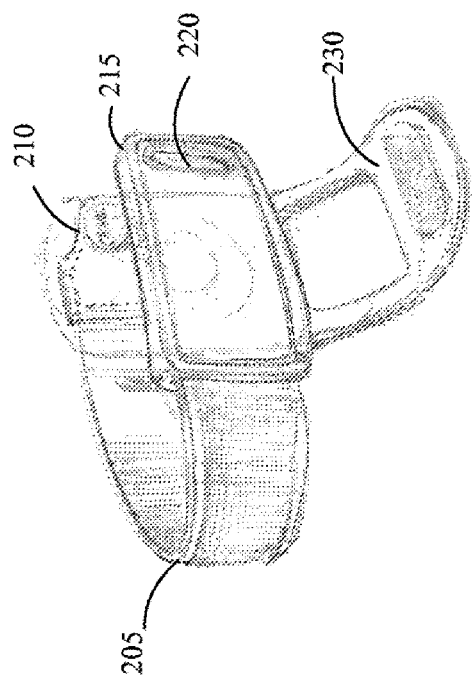
FIG. 2A
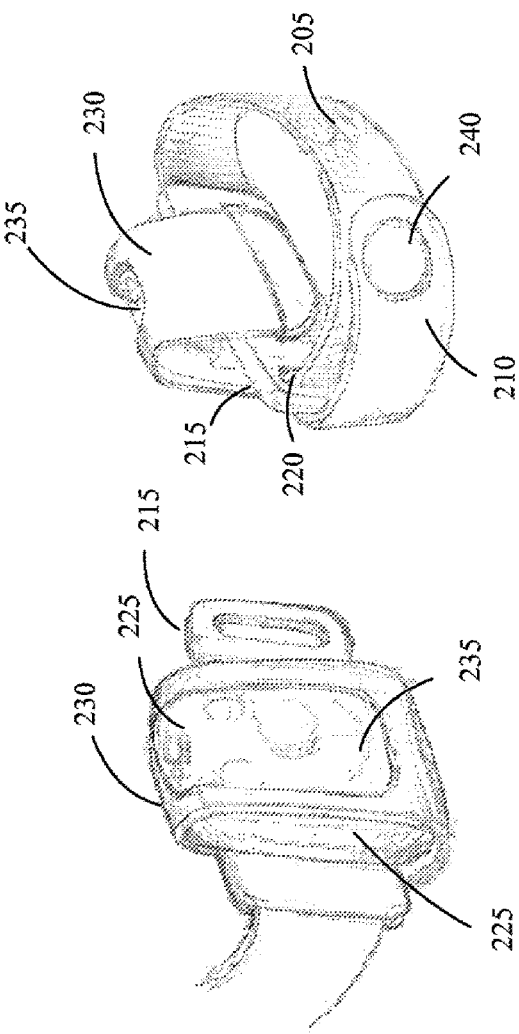
FIG. 2C
FIG. 2B

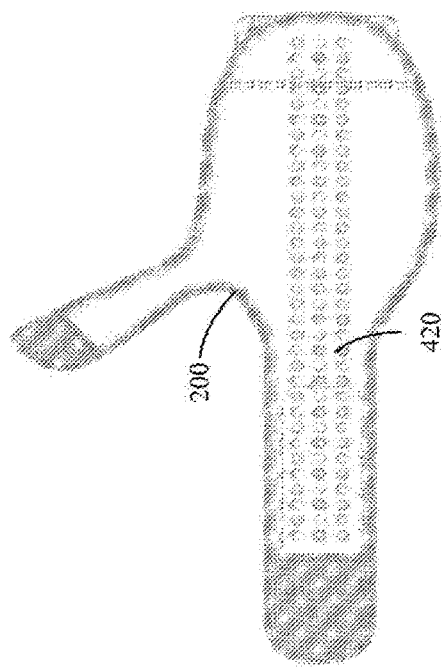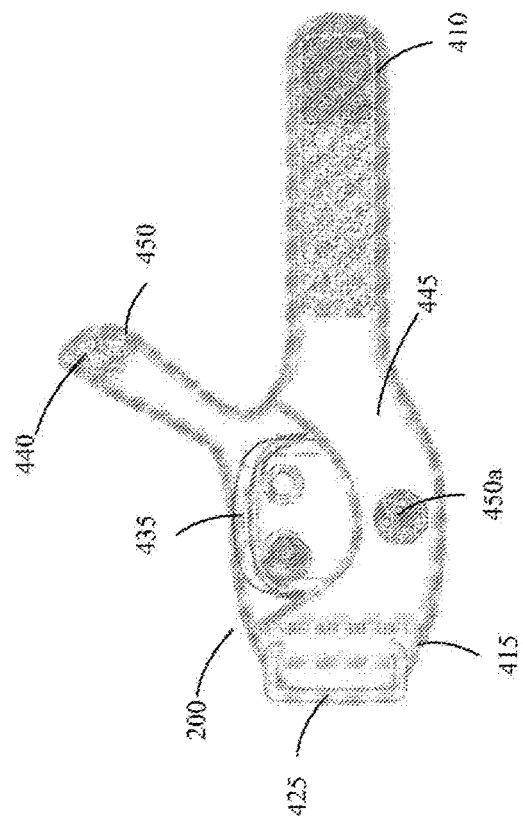

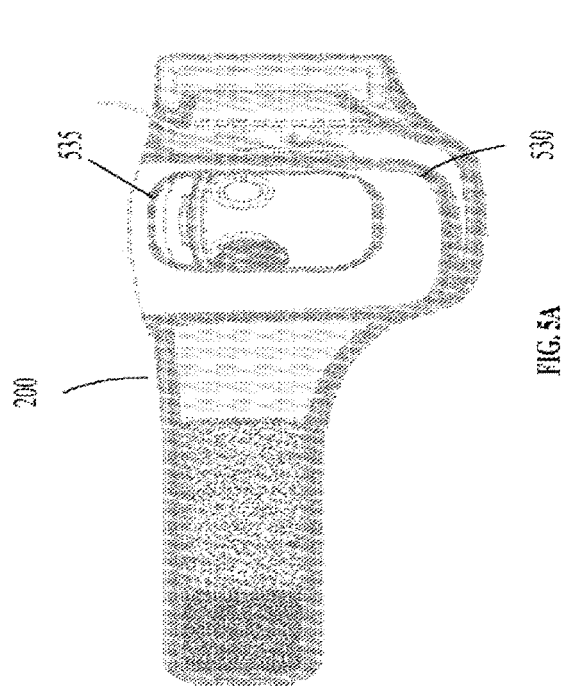
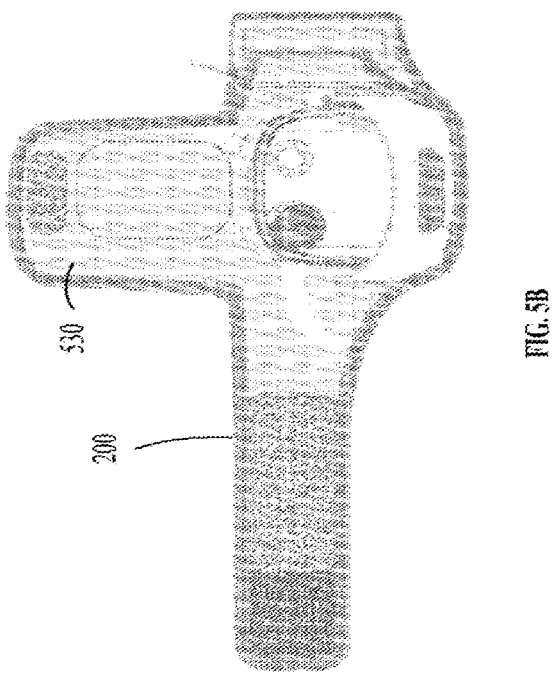
FIG. 5A
FIG. 5B

FLUID DETECTION SYSTEM

This Application is a continuation of application Ser. No. 14/958,949, filed Dec. 4, 2015, now U.S. Pat. No. 9,782,303, which itself is a continuation of application Ser. No. 13/925,859, filed Jun. 25, 2013, now U.S. Pat. No. 9,261,231. This Application claims priority to these earlier Applications to the fullest extent of the law.

FIELD

This application relates to a device for holding a fluid detection system that monitors body fluid leakages and issues alarms. More specifically, but not exclusively, this application relates to a band for securely holding an alarm associated with the fluid detection system.

BACKGROUND

Existing fluid detection alarms can be attached to a user's clothes with a safety pin, magnet, or specialized clips. Not only are these approaches limiting in nature, they can create various inconveniences for the user. Even though attaching a fluid detection alarm to the user's clothes can ensure that it is close enough to be heard, the sound can be easily muffled if the user is covered with a blanket or some other covering. Besides, the user would be forced to sleep in one position to ensure that he/she is not sleeping on the fluid detection alarm. Additionally, safety pins and specialized clips can easily impair the comfort and convenience of the user, while magnets are often not strong enough to hold a fluid detection alarm.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided is a band for holding a fluid detection system. The band may comprise a strap having a first portion, and a second portion configured to couple to the first portion forming a closed loop adjustable in diameter to fit around a body part of a wearer. The body part may include an arm, a hand, a waist, a head, a leg, a foot, a wrist, a trunk, a neck, a chest, and so forth. In one example embodiment, the band may comprise a pouch attached thereto and configured to securely hold an alarm of the fluid detection system. The band may further comprise a flap configured to form a closed loop adjustable in diameter to hold an alarm of the fluid detection system. The first portion of the band may comprise an opening to receive the second portion in order to couple the first portion and the second portion together. The alarm may include fluid sensing means to sense fluid leakage from the body of the wearer. The fluids may include sweat, water, blood, urine, feces, and so forth. On sensing the fluid leakage, notification data may be transmitted to the alarm. On receiving the notification data, the alarm may produce one or more of the following: a sound signal, a light signal, a vibration signal or a radio signal. The alarm may include an enuresis alarm, a moisture detection alarm, a potty training alarm, an incontinence alarm, a bedwetting alarm, and so forth. The fluid sensing means may be detachably disposed on the band.

In one example embodiment, the fluid sensing means may be configured to wirelessly communicate with the alarm. In other embodiments, the fluid sensing means may be connected to the alarm with wires to enable communications between the alarm and sensors.

In one example embodiment, the band may further comprise an additional alarm communicating with the fluid sensing means and located remotely from the wearer.

In one example embodiment, the band may include an anti-skid backing.

In one example embodiment, the second portion of the band, as well as the flap, may include Velcro. Alternatively, the second portion may include a magnet or a loop.

In one example embodiment, the flap may include one or more openings to provide an audibility and visibility of a signal produced by the alarm.

Provided is also a method for holding a fluid detection system on a body of a wearer. The method may start with providing a band being configured to form a closed loop with an adjustable diameter to be secured around a body part of the wearer. The method may further include securely fixing an alarm of the fluid detection system inside a pouch of the band using a flap. The flap may be configured to form a closed loop adjustable in diameter to fit the size of the alarm in the pouch.

In one example embodiment, the method may further proceed with the alarm receiving a notification data from the fluid sensing means. The notification data may be associated with the fluid sensing means sensing a fluid. On receiving the notification data, the alarm may produce one or more of the following: a sound signal, a light signal, a vibration signal, or a radio signal.

In further exemplary embodiments, modules, subsystems, or devices can be adapted to perform the recited steps. Other features and exemplary embodiments are described below.

BRIEF DESCRIPTION OF DRAWINGS

Embodiments are illustrated by way of example and not limitation in the figures of the accompanying drawings, in which like references indicate similar elements and in which:

FIG. 2A illustrates an example of a band for holding a fluid detection system with a flap folded down, in accordance to some embodiments.

FIG. 2B illustrates an example of a band for holding a fluid detection system with an alarm positioned within a flap folded up, in accordance to some embodiments.

FIG. 2C illustrates a back view of a band for holding a fluid detection system with an alarm positioned inside a flap folded up, in accordance to some embodiments.

FIG. 4A shows a back view of a band for holding a fluid detection system with a finger-shaped flap, in accordance to some embodiments.

FIG. 4B shows a front view of a band for holding a fluid detection system with a finger-shaped flap, in accordance to some embodiments.

FIG. 5A shows a front view of a band for holding a fluid detection system with a flap in the closed position, in accordance to some embodiments.

FIG. 5B shows a front view of a band for holding a fluid detection system with a flap in the open position, in accordance to some embodiments.

DETAILED DESCRIPTION

Figure 1:
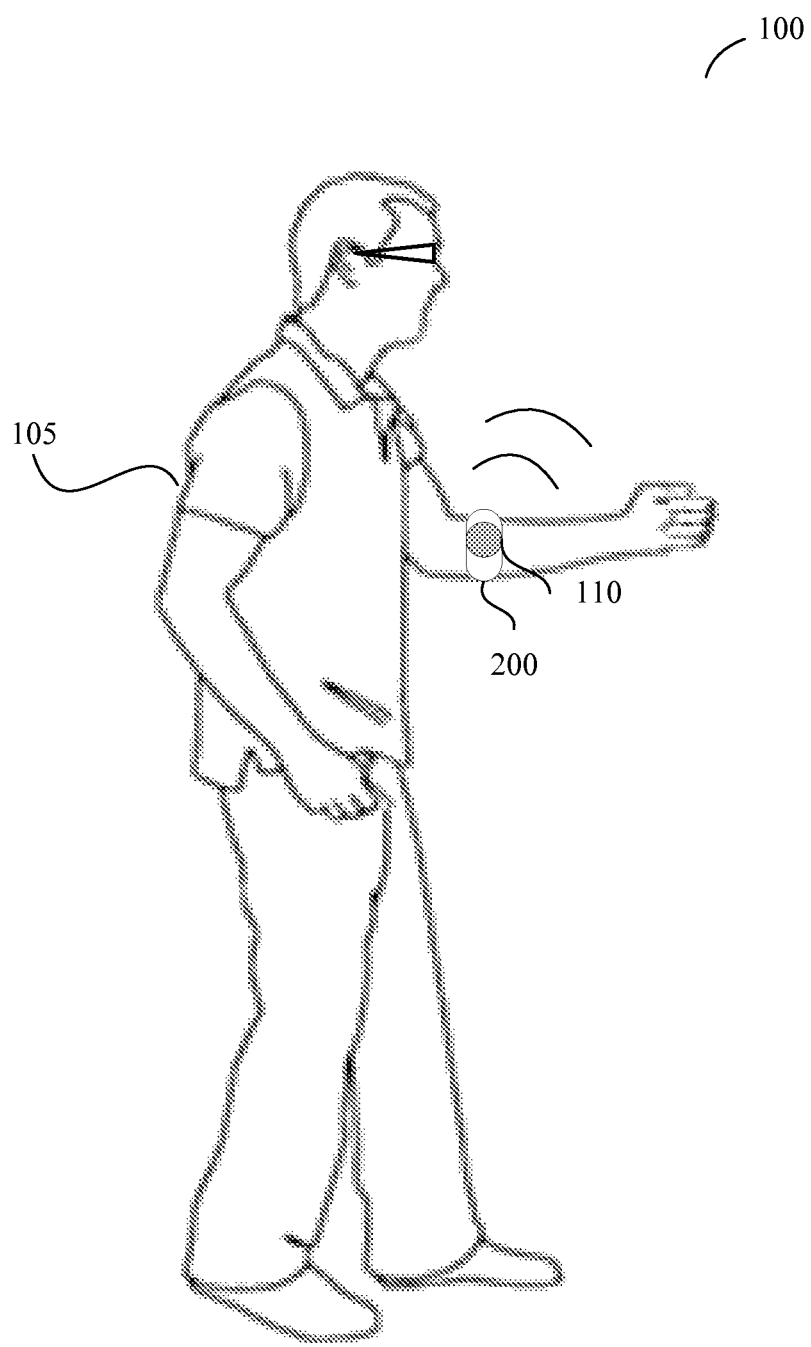
FIG. 1 illustrates an environment within which a band for holding a fluid detection system on a body of a wearer and methods of user thereof can be implemented, in accordance to some embodiments.

A band for holding a fluid detection system and related method are described herein. Specifically, the band is designed to securely hold an alarm of the fluid detection system in place so it does not move around and stays in contact with a wearer of the band. The fluid detection system may contain moisture sensors that are able to accurately detect the presence of any type of fluid or moisture including body fluids, such as sweat, water, blood, urine, feces, and so forth. The alarm of the fluid detection system may be configured to quickly alert both a wearer of the fluid detection system and medical personnel or a caretaker that a fluid leak has been detected from the wearer's body. The fluid detection system may monitor a number of fluid sensors simultaneously, which would eliminate the need for the caretaker to continuously inspect the wearer visually for potentially fatal fluid leaks.

In certain example embodiments, the band may be designed to be placed anywhere on the body of the wearer. For example, the band may be placed around an arm of the wearer as an armband, waist as a waistband, head as a headband, leg as a legband, foot as a footband, wrist as a wristband, and so forth. The wearer may easily put on the band by himself. The wearer may also have a caretaker place the band on the body of the wearer, and the caretaker may be alerted when the fluid is detected by the fluid detection system.

In certain example embodiments, the alarm of the fluid detection system may include an enuresis alarm, a moisture detection alarm, a potty training alarm, an incontinence alarm, a bedwetting alarm, and so forth. The band may be also used to hold any alarm system, wired or wireless, which can detect moisture.

In certain example embodiments, the band may be made of soft, comfortable, and breathable material, such as, for example, Neoprene, since it will be in contact with skin for an extended period of time. Additionally, the material may be hypoallergenic to avoid irritating the skin of the wearer. The band may be made of washable material and contain a stretchable fabric.

In certain example embodiments, an anti-skid backing may be provided on at least a part of the band surface to enable secure fixing of the band with the skin of the wearer. Thus, slip off of the band may be avoided.

In certain example embodiments, the band may include a simple fastening mechanism to secure the band in place around an arm/body/head/wrist/leg/foot of the wearer. The band may comprise a first portion and a second portion. The second portion may have an opening to receive the first portion and form a closed loop adjustable in diameter. In such a way, the band may be adjusted to fit around a body part of the wearer. Additionally, the band may include Velcro to attach the first portion to the second portion. Velcro may provide convenience for repeated opening and closing of the band as compared to conventional alarm fastening methods, such as safety pins or clips.

In certain example embodiments, the band may include a pouch to securely place the alarm inside and a flap to cover the alarm and hold it securely in place. The flap may be attached to the band near the pouch such that the flap may cover the alarm positioned inside the pouch and be connected to the outside surface of the pouch. Both the flap and the pouch may comprise Velcro to be connected to each other to form a closed loop. Upon connecting the flap to the pouch, a diameter of the closed loop may be regulated to fit the size of an alarm placed inside the pouch. Thus, the band is configurable to accommodate small and large alarms.

In certain example embodiments, the flap may be provided with one or more openings in order for the wearer to hear the alarm and see the light signals.

Thus, the band for holding a fluid detection system described herein provides a simple, economical, safe means for accommodating various types of fluid sensing alarms anywhere on the body of the wearer. The band provides increased comfort to the wearer due to simplified mounting, positioning, and removing procedures.

Referring now to the drawings, FIG. 1 illustrates an environment 100 within which a band 200 for holding a fluid detection system on a body of a wearer and a method of use thereof can be implemented. FIG. 1 shows a wearer 105 wearing a band 200 about his arm. The band 200 securely holds the fluid detection system 110, which includes a fluid detection alarm operatively coupled to the fluid sensing means. The fluid detection means may be wired to the alarm. Alternatively, the fluid sensing means may be wirelessly connected with the alarm. In some example embodiments, the fluid sensing means may be detachably disposed on the band 200.

The alarm may be configured to receive a notification data from the fluid sensing means upon sensing a fluid. On receiving the notification, the alarm may produce a signal to the wearer 105 to warn the wearer about the fluid leakage.

In certain example embodiments, the band 200 may be also used for assisting in the prevention of diaper rash, for potty training of infants, in curing enuretic youngsters, and for detecting the leakage of blood or other fluids after surgery and invasive diagnostic procedures. The band 200 may also be used to monitor and record urinary incontinence.

In certain example embodiments, the band 200 may be useful for detecting leaks in domestic hot water heaters or other liquid storage devices.

In certain example embodiments, the band 200 may be configured such that it may be attached to practically any body part of the wearer 105. The band 200 may comprise a strap and two portions, a first and a second, which may be easily coupled such that the band 200 forms a closed loop. The coupling may be easily released. In some example embodiments, the coupling may be implemented via Velcro provided on a surface of the strap and at least on one of the first and second portions. In some example embodiments, the closed loop may be adjustable to a range of diameters of, for example, approximately one to fifteen inches.

In some example embodiments, the wearer 105 may wear the band 200 with an alarm positioned inside the band 200 while walking, running, resting, or sleeping. He may perform any movement and action without a risk of the band slipping off, since the band is configured to be securely fixed on a body part of the wearer. Additionally, due to the adjustable diameter, the band may be tightly fitted to a body part of the wearer, or it may be slightly loosened for comfortable sleep.

As shown, the alarm may be configured to generate a signal upon detecting any type of fluid or moisture on the surface of the body or garments of the wearer. The signal may be of different types, such as a sound, a light, a vibration, a radio signal, and so forth. In certain example embodiments, an additional alarm may be provided. The additional alarm may communicate with the fluid sensing means and be located remotely from the wearer 105. For example, the additional alarm may be provided to a caretaker who will be alerted when a fluid is detected by the fluid sensing means disposed on the wearer 105. The additional alarm may be configured to wirelessly receive signals from the alarm disposed on the wearer 105.

FIG. 2A illustrates an example of a band for holding a fluid detection system with a flap folded down, in accordance to some embodiments. As shown, the band 200 may comprise a strap 205 including soft, flexible material, such as neoprene, forming a first portion 215 and a second portion 210. Various other types of materials may be alternatively used including, but not limited to, leather, cotton, polyester, plastic, nylon, vinyl, synthetic leather, rubber, and so forth. An opening 220 may be provided in the first portion 215. The opening 220 may be configured to fit in the second portion 210 to pass through the opening 220 and be fixed to an intermediate portion of the strap 205, thereby forming a closed loop. The second portion 210 may be slightly tapered to fit into the opening 220. At least a portion of the strap 205 and the second portion 210 may include Velcro. Upon insertion of the second portion 210 into the opening 220, the second portion 210 may be dragged through the opening 220 until a desired diameter of the loop is achieved. The second portion 210 may be then attached to a Velcro portion of the strap 205.

FIG. 2B illustrates an example of a band for holding a fluid detection system with an alarm positioned within a flap folded up, in accordance to some embodiments. As shown, a flap 230 may be attached to a front bottom of the first portion 215. In its folded up position, the flap 230 may encircle an alarm 235 and be attached to the back of the first portion 215 by means of Velcro or any other suitable fastening means. The flap 230 includes one or more front and side openings 225. The openings 225 may coincide in position with signal emitting components including, but not limited to light-emitting diodes (LEDs). Such a configuration of the flap 230 may provide better audibility and visibility of emitted signals for the wearer.

Additionally, the openings 225 may provide access to various ports that the fluid detection system may have. Additionally, the openings may be used to attach one or more sensors with wires.

In some example embodiments, the band 200 may include elastic stretch material, which expands when being fitted to an arm or leg of the wearer and then contracts to ensure secure holding of the band on the body of the wearer. The band may be adjustable to various degrees of tightness on various body parts of the wearer.

FIG. 2C illustrates a back view of a band for holding a fluid detection system with an alarm accommodated therein, in accordance to some embodiments. As shown, the second portion 210 may pass through the opening 220 of the first portion 215. The first portion 215 may then be folded and be fixed to the strap 205 by Velcro 240, thus forming a loop. The flap 230 may fold over the alarm 235, thereby forming a pouch to hold the alarm 235, and be fixed to the back side of the first portion 215, for example, by Velcro.

Figure 3:
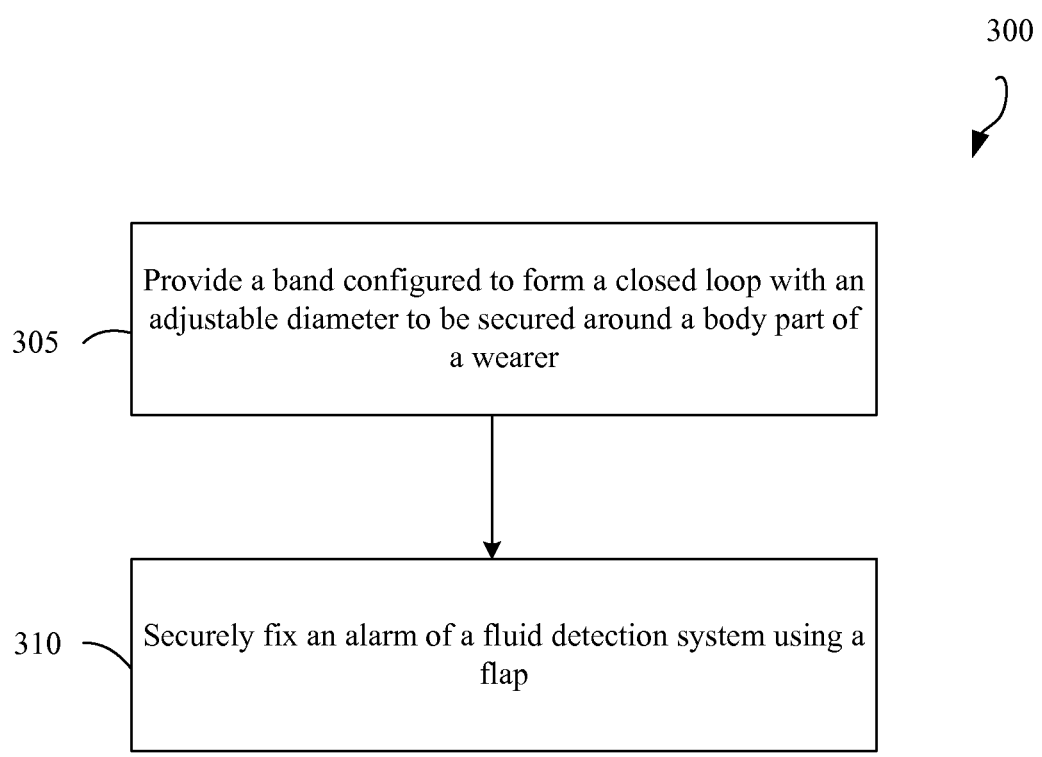
FIG. 3 is a flow chart illustrating a method for holding a fluid detection system on a body of a wearer, in accordance with certain embodiments.

FIG. 3 is a flow chart illustrating a method for holding a fluid detection system on a body of a wearer, in accordance with certain embodiments. The method 300 starts with providing, at operation 305, a band being configured to form a closed loop with an adjustable diameter to be secured around a body part of the wearer. The method 300 may further proceed with securely fixing an alarm of the fluid detection system inside a pouch of the band at operation 310. The alarm may be fixed using a flap or otherwise. In various embodiments, the flap may form a pouch to fix the alarm. Alternatively, the strap may include a pouch with a flap to fix the alarm in the pouch. The flap may be configured to form a closed loop that is adjustable in diameter to fit the size of the alarm in the pouch.

In certain example embodiments, the alarm may be configured to receive notification data from the fluid sensing means. The notification data may be associated with the fluid sensing means sensing a fluid. Upon receiving the notification data, a signal may be produced by the alarm. The signal may include one or more of the following: a sound signal, a light signal, a vibration signal, a radio signal, and so forth.

FIG. 4A shows a back view of a band for holding a fluid detection system with a finger-shaped flap, in accordance to some embodiments. As shown, an anti-skid backing 420, formed of a plurality of knobs, may be provided on the back surface of the band 200. The anti-skid backing 420 may prevent the band 200 from moving around and slipping of a body part of a wearer.

FIG. 4B shows a front view of a band for holding a fluid detection system with a finger-shaped flap, in accordance to some embodiments. As shown, an elongated ring 425 may be attached to a first portion 415 of the band 200. The ring 425 may function in the same way as the opening 220 on FIG. 2, i.e., receive a second portion 410 of the band 200 to form a closed loop. The ring 425 may be made of nylon, plastic, or other suitable materials and may have different forms and sizes. Additionally, a pouch 445 may be provided on the first portion 415 of the band 200 to accommodate an alarm 435. In this example embodiment, the pouch 445 has a U-shaped cut at its top, which uncovers a portion of the alarm 435. A special finger-shaped design of a flap 440, at its folded up position, together with the U-shaped cut of the pouch 445, form two openings, through which a light signal or a sound signal may penetrate. The flap 440 may include a Velcro portion 450, which may be fixed to a corresponding Velcro portion 450a disposed on an outer side of the pouch 445.

FIGS. 5A and 5B both illustrate a front view of the band for holding a fluid detection system with a flap in its open and closed positions, in accordance to some embodiments. FIGS. 5A and 5B show the band 200 similar to that shown in FIGS. 4A and 4B except for the shape of a flap 530. The flap 530 in FIGS. 5A and 5B may be rectangular with one or more openings. The openings may occupy the major portion of the flap 530 to avoid suppressing sound or light signal and to ensure that a wearer can hear a sound signal and see a light signal.

Thus, a band for holding a fluid detection system and various methods of use thereof have been described. Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. A fluid detection device, comprising:
a fluid sensor positioned near a patient's body and providing a signal whether the sensor detects fluid from the patient's body;
an alarm coupled to the fluid sensor, the alarm including one or more of: an audible signal sensible by the patient, a haptic signal sensible by the patient, a visible signal sensible by the patient;

a casing surrounding the alarm and allowing the signal to be sensed by the patient through the casing; and a fastener coupled to the casing, adjustable to attach and remove from one or more of:

the patient's body, a patient's clothing.

2. The fluid detection device as in claim 1, wherein the casing, when closed, couples a power source to the alarm.

3. The fluid detection device as in claim 1, including a human interface coupled to the alarm, the human interface being accessible to the patient while the fastener is attached to the patient's body or the patient's clothing.

4. The fluid detection device as in claim 1, wherein the alarm is coupled to the fluid sensor using a physical connection.

5. The fluid detection device as in claim 1, wherein the fastener includes a stretchable loop disposed to be closed around one or more of: a portion of the patient's body, a portion of the patient's clothing.

6. The fluid detection device as in claim 1, wherein the fastener is adjustable to at least one or more of: a looser mode, a tighter mode.

7. The fluid detection device as in claim 1, wherein the fastener includes one or more of a loop disposed to be closed around one or more of: a portion of the patient's body, a portion of the patient's clothing;

an element including a first end and a second end, the first end disposed to be coupled to the second end to secure a loop around one or more of: a portion of the patient's body, a portion of the patient's clothing.

8. A method of fluid detection, including steps of positioning a fluid sensor near a patient's body;

coupling an alarm to the fluid sensor, and whenever the sensor detects fluid from the patient's body, providing a signal from the fluid sensor to the alarm for indicating detection of the fluid;

whenever the alarm receives the signal from the fluid sensor, providing one or more of:

an audible signal sensible by the patient, a haptic signal sensible by the patient, a visible signal sensible by the patient through a casing;

positioning the alarm into the casing affixed to the patient's body by a fastener, wherein the fastener is adjustable to attach and remove from one or more of: the patient's body, a patient's clothing.

9. The method as in claim 8, including steps of providing a human interface coupled to the alarm, the human interface being accessible to the patient while the fastener is attached to the patient's body or the patient's clothing.

10. The method as in claim 8, including steps of providing a physical connection between the alarm and the fluid sensor.

11. The method as in claim 8, including steps of providing the fastener with a looser mode and a tighter mode.

12. The method as in claim 8, including steps of providing the fastener with a loop disposed to be closed around one or more of: a portion of the patient's body, a portion of the patient's clothing.

13. The method as in claim 12, wherein the loop is stretchable.

14. The method as in claim 8, including steps of providing the fastener with an element including a first end and a second end, the first end disposed to be coupled to the second end to secure a loop around one or more of: a portion of the patient's body, a portion of the patient's clothing.

15. The method as in claim 8, wherein the casing, when closed, couples a power source to the alarm.

\* \* \* \* \*